United States Patent [19]

Hartmann et al.

[11] 4,073,802

[45] Feb. 14, 1978

[54] PROCESS FOR THE PREPARATION AND PURIFICATION OF 3-(4-LITHIOSULFOPHENOXY)-1,2-PROPANEDIOL

[75] Inventors: Ludwig Albert Hartmann; Richard Lowell West, both of Wilmington, Del.

[73] Assignee: ICI Americas Inc., Wilmington, Del.

[21] Appl. No.: 724,028

[22] Filed: Sept. 16, 1976

[51] Int. Cl.$^2$ .................................... C07C 143/46
[52] U.S. Cl. ...................................... 260/512 R
[58] Field of Search ............................ 260/512 R

[56] References Cited

U.S. PATENT DOCUMENTS 3,706,712  12/1972  Davis et al. .................... 260/75 S Primary Examiner—Nicky Chan

[57] ABSTRACT

An improved process for the preparation of 3-(4-lithiosulfophenoxy)-1,2-propanediol relatively free from inorganic impurities is represented wherein the subject material is made by reacting lithiosulfophenol with either glycerol monochlorhydrin or epichlorohydrin in aqueous solution in the presence of an alkaline calcium compound and thereafter purifying by removing the calcium sulfate and hydrochloric acid from the aqueous reaction media. The subject material can be obtained at purities of 98% in yields exceeding 70%.

8 Claims, No Drawings

PROCESS FOR THE PREPARATION AND PURIFICATION OF 3-(4-LITHIOSULFOPHENOXY)-1,2-PROPANEDIOL

The invention is directed to the preparation and purification of 3-(4-lithiosulfophenoxy)-1,2-propanediol from aqueous solutions containing difficultly removable chloride salts. Specifically, the invention relates to the preparation of the subject material by reacting lithiosulfoxyphenol with glycerol monochlorohydrin [3-chloro-1,2-propanediol] or epichlorohydrin in aqueous medium in the presence of alkaline calcium compounds. The product is purified by removal of calcium chloride in the form of calcium sulfate and hydrochloric acid.

Pure 3-(4-lithiosulfophenoxy)-1,2-propanediol [lithium-p-(2,3-dihydroxypropoxy)benzenesulfonate] is used as a co-monomer in the preparation of dyeable polyester resins employed in the textile industry. It displaces up to 5% of the glycol normally employed in the manufacture of diacid-diol condensation resins. Typical procedures for the preparation of modified synthetic polyesters are presented in U.S. Pat. No. 3,706,712 wherein 3-(4-lithiosulfophenoxy)-1,2-propanediol is prepared by the reaction of glycerol chlorohydrin with a lithium salt of p-phenolsulfonic acid in aqueous solution. The subject product is recovered by flashing off water by vacuum evaporation, filtration and a series of recrystallization steps using a 9/1 isopropanol/water solution. Pure product is obtained in economically unacceptable yields of 38%.

It is an object of the present invention to present a process for preparing 3-(4-lithiosulfophenoxy)-1,2-propanediol in yields in excess of 70% and having purities of at least about 98%.

In the process of the invention the monolithium salt of phenol sulfonic acid is reacted with glycerol chlorohydrin or epichlorohydrin in aqueous medium in the presence of alkaline calcium compounds such as calcium oxide, calcium hydroxide, calcium acetate, and the like, to form 3-(4-lithiosulfophenoxy)-1,2-propanediol and by-product calcium chloride. Sulfuric acid is added to the aqueous mixture to form calcium sulfate and hydrochloric acid. The calcium sulfate is removed by filtering. Hydrochloric acid is thereafter removed by vacuum-stripping, and subsequent reslurrying, filtering, washing, and drying the product.

More specifically, the process is carried out by preparing a slurry of the calcium compound, preferably calcium hydroxide in deionized water in concentrations ranging from 2–20%. To a slurry prepared in this manner at least 1 mol of lithium p-phenolsulfonate is added to the mix for each ½ mol of calcium present. The slurry is then heated to a temperature in the range of 50°–85° C. Either 3-chloropropanediol [glycerol chlorohydrin] or epichlorohydrin, which undergoes hydrolysis to glycerol chlorohydrin in aqueous medium, is slowly added with agitation. The temperature is raised to reflux temperature, that is about 102° C., and held at that temperature for 2–4 hours until the solution becomes clear.

The solution is thereafter cooled to about 50°–85° C. and concentrated sulfuric acid is then added. The slurry is then cooled to room temperature or below and mixed with an organic co-solvent such as methanol, ethanol, isopropanol, or the like, and permitted to stand until at least 90% of the calcium sulfate formed therein precipitates.

After calcium sulfate is removed by filtration, the filtrate is vacuum-stripped at about 50°–60° C. to remove HCl and low boiling organic solvent.

The semi-solid residue is thereafter slurried with an organic solvent such as isopropyl alcohol, filtered, and washed several times with organic solvent to remove impurities. The filter cake is vacuum dried at about 85° C. at pressures less than 1 mm. to produce the subject product in yields exceeding 70% and having chloride ion concentrations less than 0.1% by weight. The presence of high concentrations of chloride ion found in material made by other routes causes stress corrosion in the polymerization reactors employed to make the modified polyester resins containing the lithium salt. Processes wherein lithium chloride by-product is a contaminant are particularly difficult to purify since the solubility of lithium chloride is very close to that of the product.

The reaction is best carried out by using stoichiometric amounts of lithium p-phenolsulfonate, calcium hydroxide and 3-chloropropanediol. There is no advantage in the use of larger amounts of calcium hydroxide or alkaline calcium equivalents because more sulfuric acid would be required for neutralization and most likely larger amounts of calcium would be retained by the product. There is no improvement or advantage offered by the use of smaller amounts or greater amounts than stoichiometric of the phenolsulfonate or the propanediol starting materials. Best yields are obtained when equimolar amounts of the major reactants are used.

In the formation of aqueous slurries of the reacting ingredients the least amount of water needed to carry out the reaction is preferred. Additional amounts of water can be used; however, more organic co-solvent will be required to precipitate calcium sulfate quantitatively from the aqueous medium in which the reaction is carried out.

Either concentrated or 2–5 N sulfuric acid may be used conveniently. The addition of the organic co-solvent such as methanol or isopropyl alcohol to the aqueous medium assures more complete precipitation of calcium sulfate. Isopropyl alcohol is preferred at a ratio of 2 parts to 1 part water. Good results are generally obtained with a range of 1–3 parts isopropyl alcohol per 1 part water. More isopropyl alcohol can be used but becomes uneconomical and at very high alcohol concentrations product precipitates out with calcium sulfate. Use of less isopropyl alcohol is not recommended since calcium sulfate precipitation will be incomplete thus contaminating the product. Other water miscible solvents can be used such as methanol, ethyl alcohol, n-propyl alcohol, acetone, dioxane, and ethylene glycol. If methanol is used, the preferred ratio is 3 parts to 1 part water. The other organic co-solvents may be expected to be effective in similar proportions.

Vacuum-stripping of the product is somewhat critical only with regard to the yield of product which can be obtained. Generally, it is advisable to vacuum-strip the aqueous isopropyl alcohol solutions until a semi-solid mass is obtained which contains about 30% water. Enough isopropyl alcohol is then added to cause product precipitation and to yield a composition near 90% aqueous alcohol at which concentration the best product yields are obtained. Better yields might be obtained when less water is present but handling of the product becomes difficult. The preferred ratio of solids to solvent at the time of crystallization is about 0.2 to 1.0.

The final washing of the crystallized product is done to remove hydrochloric acid. This can be accomplished with any solvent in which the product is not soluble such as alcohols, ketones, esters, aromatic hydrocarbons, and chlorinated solvents, such as chloroform and ethylene chloride. While isopropyl alcohol has been employed in the examples, the other solvents in the above list can be used in proportions equivalent to 50-100% of those employed for isopropyl alcohol.

The following examples demonstrate the application of the invention with varying degrees of efficiency and are not considered to be limiting in scope.

EXAMPLE 1

Into a 250 milliliter 3-neck flask provided with a thermometer, stirrer and condenser is added an aqueous slurry containing 3.7 grams (0.05 mols) of calcium hydroxide, 18.0 grams (0.1 mol) lithium p-phenolsulfonate, and 50 milliliters of water. The slurry is heated to 60°-65° C. and admixed with 11.05 grams (0.1mol) 3-chloropropanediol over a period of 30 minutes. The temperature of the mixture is then raised to 102° C. (reflux temperature) and held for a period of 3.5 hours. The clear solution is then cooled to 60°-75° C. and admixed with 21.6 mls. of 4.625 N (0.1 mol) sulfuric acid. The slurry is cooled to room temperature, diluted with 200 mls. methanol and allowed to remain standing for 20 hours at room temperature. Calcium sulfate is filtered, washed with a minor portion of methanol and dried. The recovered calcium sulfate amounts to 98.6% of theoretical. The filtrate containing product is gradually vacuum-stripped at a temperature of 50°-60° by aspiration to a final pressure to 20 mms. After aspiration, the residue remaining in the flask is a semi-solid mass weighing 31.6 grams. The product is then treated with 100 mls. isopropyl alcohol under high shear mixing conditions and filtered. The crude filter cake is washed with 50 mls. isopropyl alcohol. It is thereafter washed with six portions of 15 ml. isopropyl alcohol and vacuum dried at 85° C. at less than 1 mm. pressure for 3 hours. The yield of product is 17.8 grams or 70.1% of theoretical and has analysis as follows:

$Cl^- = 0.01\%$
$SO_4^= = 1.45\%$
$OH\# = 508$

Periodate Consumption = 7.18 meq./g
$Ca^{++} = 0.9\%$
$Li^+ = 2.6\%$
pH (20%) = 5.3

EXAMPLE 2

A suspension is prepared in a 2 liter flask with 37.0 grams $Ca(OH)_2$ and 500 ml. water. Lithium p-phenolsulfonate (180.0 grams) is added with slight cooling and the suspension is heated at 60°. 3-Chloropropanediol (116.5 grams) is added from a dropping funnel at 60° over a period of 50 minutes and then the hazy solution is heated for 5 hours at 102°. Clearing takes place and the pH is 6.0. The solution is cooled and acidified with 216 ml. of 4.625 N sulfuric acid and diluted with 1 liter isopropyl alcohol. The calcium sulfate is filtered off after 16 hrs. and washed with about 100 ml. isopropyl alcohol. The yield of calcium sulfate is 65.8 grams (96.6%) after drying at 90°/1 mm. for 18 hrs. The filtrate is vacuum-stripped, initially at bath temperature of 40°-70°/90-120 mm. and later at 60°-70°/15-20 mm. until 360 g. residue remains which is still stirrable at 60°. This product is dispersed at 60° in about 900 ml. isopropyl alcohol and is then kept near 0° for 16 hrs. The product is filtered off and washed with 650 ml. isopropyl alcohol. Preliminary drying is at 60°/atmospheric pressure and final drying is at 95°/1 mm. for 17 hrs. The yield is 186.1 grams (73.3%). Analysis is as follows:

$OH\# = 460$
$IO_4^-$ consumption = 7.26 meq./g
$Ca^{++} = 0.6\%$
$SO_4 = 1.36\%$
$Cl = 0.089\%$ The filtrate from the main portion of product is evaporated to a volume of about 200 ml. and a slurry is obtained. The solids are filtered off, washed with 300 ml. isopropyl alcohol, and dried at 65°/atmospheric pressure and at 92°/1 mm. for 8 hrs. The yield of the second crop is 12.0 grams (4.72%). Total yield of product from both crops is 78%. Analysis is as follows:

$Cl^- = 0.075\%$
$SO_4^= = $ nil
$OH\# = 452$
Periodate consumption — 7.17 meq./g.

EXAMPLES 3-6

Results of additional examples listed in Table I were carried out according to the procedures of Examples 1 and 2 and illustrate the chloride analyses obtained in a series of similar runs. Calcium sulfate is precipitated in aqueous medium (Examples 3 and 4) and in aqueous alcoholic medium (Examples 5 and 6) in these examples, and the data allow a comparison of product composition after modifying the work-up by addition of alcohol.

TABLE I

| EXAMPLE | 3 | 4 | 5 | 6 |
|---|---|---|---|---|
| Ca(OH)$_2$ | 3.70g | 3.70g | 3.70g | 3.70g |
| Mols | 0.05 | 0.05 | 0.05 | 0.05 |
| H$_2$O | 60 ml | 30 ml | 70 ml | 50 ml |
| Li P-phenolsulfonic acid | 18.0g | 18.0g | 18.0g | 18.0g |
| Mols | 0.1 | 0.1 | 0.1 | 0.1 |
| 3-Chloropropanediol | 11.05g | 11.05g | 11.05g | 11.65g |
| Mols | 0.1 | 0.1 | 0.1 | 0.105 |
| Time at 60° | 13 min. | 28 min. | 20 min. | 50 min. |
| Time at 102° | 11 hrs. | 4 hrs. | 7 hrs. | 5 hrs. |
| pH (end of reaction) | 7.8 | 6.8 | 6.5 | 6.5 |
| H$_2$SO$_4$ (3.178N) | 31.5 ml | — | — | — |
| H$_2$SO$_4$ (4.625N) | — | 21.6 ml | 21.6 ml | 21.6 ml |
| Diluent Isopropyl Alcohol | None | None | MeOH,100ml | IPA,100ml |

TABLE I-continued

| EXAMPLE | 3 | 4 | 5 | 6 |
|---|---|---|---|---|
| Added to Residue Isopropyl Alcohol | 75 ml | 190 ml | 150 ml | *75 ml |
| (product wash) | 75 ml | 90 ml | 75 ml | *75 ml |
| Product Dried At | 60°/3 days | 75°/1mm/16hr | 86°1/mm/16 hr | 95°/1mm/17hr |
| $CaSO_4$ Separated | — | 4.88g | 6.07g | 6.41g |
| (%) of calculated | — | 71.7 | 89.2 | 93.3 |
| Product Yield | 18.7g | 19.6g | 16.24 g | 15.9g |
| (%) | 73.6 | 77.1 | 64.0 | 62.6 |
| Analysis | | | | |
| $Cl^-$ (%) | 1.025 | 0.035 | 0.02 | 0.085 |
| $SO_4^=$ (%) | 6.04 | 6.60 | 2.94 | 1.67 |
| OH# | — | — | 473 | 504 |
| $IO_4^-$ (meg/g) | — | — | 7.08 | 7.20 |
| $Ca^{++}$ (%) | 2.7 | 3.2 | 1.6 | 0.87 |
| $Li^{++}$ (%) | — | — | — | — |
| pH (20%) | 5.0 | 4.7 | 5.4 | 6.2 |

*2/1 methyl ethyl ketone/isopropyl alcohol

If lower concentrations of calcium sulfate are required, the products of Examples 1–6 can be purified through ion exchange techniques by passing aqueous solutions through an absorption column.

EXAMPLE 7

A 10 gram sample of product from Example 6 is dissolved in water to yield 112 ml. solution. A 10% aliquot is diluted to 50 ml. and analyzed for $Ca^{++}$ (166 pmm $Ca^{++}$).

The remainder of the sample (90%) is passed through a column of Amberlite IR-120- C.P. which has been converted to the lithium form by successive treatments with 5% sulfuric acid solution, water and 10% lithium chloride solution. The eluate is diluted with water to give the same concentration as the analytical reference sample which is not subjected to ion exchange. The calcium analysis showed 0.72 ppm $Ca^{++}$. Evaporation and vacuum-drying at 90°/1 mm. gave 8.50 grams of product (94.4% recovered). Ca content on dry basis is 0.0042%.

What is claimed is:

1. The process for preparing 3-(4-lithiosulfophenoxy)-1,2-propanediol from lithium p-phenolsulfonate and a compound selected from the group consisting of glycol chlorohydrin and epichlorohydrin in aqueous medium which comprises the steps of:
   (1) reacting said sulfonate and compound in the presence of substantially stoichiometric amounts of an alkaline calcium compound selected from the group consisting of calcium oxide, calcium hydroxide and calcium acetate to form by-product calcium chloride and 3-(4-lithiosulfophenoxy)-1,2-propanediol,
   (2) forming calcium sulfate and liberated hydrochloric acid by the addition of sulfuric acid,
   (3) removing precipitated calcium sulfate,
   (4) removing the liberated hydrochloric acid from the aqueous medium by vacuum-stripping until a semi-solid mass is obtained, and
   (5) recovering relatively pure 3-(4-lithiosulfophenoxy)-1,2-propanediol product from said semi-solid mass substantially free of chloride ion by recrystallization.

2. A process of claim 1 wherein said calcium sulfate is precipitated from said aqueous medium in the presence of an organic water miscible co-solvent.

3. A process of claim 2 wherein said co-solvent is selected from the group consisting of methanol, ethanol, isopropyl alcohol, n-propyl alcohol, acetone, methyl ethyl ketone, dioxane, ethylene glycol and mixtures thereof.

4. A process of claim 1 wherein said product of Step 5 is further freed from chloride ion by crystallization in the presence of an organic solvent, followed by filtration and solvent wash.

5. A process of claim 4 wherein said organic solvent is selected from the group consisting of methanol, ethanol, n-propyl alcohol, isopropyl alcohol, acetone, ethyl acetate, benzene, chloroform and ethylene dichloride.

6. A process of claim 1 wherein minor amounts of calcium remaining in the product of Step 5 are removed from an aqueous solution of said product by cationic exchange with $Li^+$ on ion exchange media.

7. A process of claim 1 wherein step (4) is carried out at about 50°–60° C. in the presence of low boiling organic solvent.

8. A process of claim 7 wherein said low boiling organic solvent is isopropyl alcohol.

* * * * *